United States Patent
Schwint et al.

(10) Patent No.: US 9,744,475 B2
(45) Date of Patent: Aug. 29, 2017

(54) BUTADIENE EXTRACTION PROCESS

(71) Applicant: Lummus Technology Inc., Bloomfield, NJ (US)

(72) Inventors: Kevin John Schwint, Long Valley, NJ (US); Robert J. Brummer, Wharton, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 56 days.

(21) Appl. No.: 15/059,771

(22) Filed: Mar. 3, 2016

(65) Prior Publication Data

US 2016/0184732 A1 Jun. 30, 2016

Related U.S. Application Data (62) Division of application No. 14/058,637, filed on Oct. 21, 2013, now Pat. No. 9,296,667.

(Continued)

(51) Int. Cl.
*B01D 3/40* (2006.01)
*C07C 7/08* (2006.01)
(Continued)

(52) U.S. Cl.
CPC .............. *B01D 3/40* (2013.01); *B01D 3/143* (2013.01); *B01D 19/0068* (2013.01); *C07C 7/08* (2013.01)

(58) Field of Classification Search
None
See application file for complete search history.

(56) References Cited

U.S. PATENT DOCUMENTS 3,345,285 A * 10/1967 MacQueen ........... C07C 11/167
208/130
4,038,156 A * 7/1977 Knott ..................... C07C 7/08
203/45

(Continued)

FOREIGN PATENT DOCUMENTS

JP H04-312536 A 11/1992
JP 2003-524585 A 8/2003

(Continued)

OTHER PUBLICATIONS

International Search Report and Written Opinion mailed Jan. 23, 2014 in corresponding Intenrational Application No. PCT/US2013/065056 (8 pages).

(Continued)

*Primary Examiner* — Tam M Nguyen
(74) *Attorney, Agent, or Firm* — Osha Liang LLP (57) ABSTRACT

A process for recovering 1,3-butadiene from a $C_4$ fraction, where the butadiene extraction processes may be operated at an intermediate pressure using a liquid ring type compressor. The use of a liquid ring compressor, among other process options presented herein, may advantageously reduce capital and operating costs, similar to the compressorless option, while mitigating the risks associated with the higher operating temperatures and pressures associated with the compressorless option. Thus, the embodiments of the processes disclosed herein encompass the best features of the conventional design (low pressure, with a compressor) with the advantages of the compressorless design (low capital and operating cost), as well as other advantages unique to the systems disclosed herein.

19 Claims, 5 Drawing Sheets

Related U.S. Application Data (60) Provisional application No. 61/720,038, filed on Oct. 30, 2012.

(51) Int. Cl.
*B01D 3/14* (2006.01)
*B01D 19/00* (2006.01)

(56) References Cited

U.S. PATENT DOCUMENTS

| | | | |
|---|---|---|---|
| 4,049,742 A | 9/1977 | Weitz et al. | |
| 4,091,046 A * | 5/1978 | Dixon | C07C 11/18 585/315 |
| 4,134,795 A * | 1/1979 | Howat, III | C07C 7/08 203/53 |
| 4,162,198 A * | 7/1979 | Stockburger | B01D 3/40 203/23 |
| 4,310,388 A | 1/1982 | Volkamer et al. | |
| 4,553,983 A | 11/1985 | Baker | |
| 5,242,550 A | 9/1993 | Asselineau et al. | |
| 5,680,775 A * | 10/1997 | Manley | F25J 3/0219 62/630 |
| 6,337,429 B1 | 1/2002 | Kindler et al. | |
| 6,395,952 B1 * | 5/2002 | Barchas | C10G 70/02 585/809 |
| 7,132,038 B2 | 11/2006 | Bohner et al. | |
| 7,226,527 B2 | 6/2007 | Bohner et al. | |
| 7,393,992 B2 | 7/2008 | Hill et al. | |
| 7,482,500 B2 | 1/2009 | Johann et al. | |
| 7,692,053 B2 | 4/2010 | Heida | |
| 8,252,150 B1 | 8/2012 | Hsu et al. | |
| 8,293,960 B2 | 10/2012 | Arnold et al. | |
| 2006/0235257 A1 * | 10/2006 | Bridges | C07C 7/08 585/810 |
| 2008/0228019 A1 * | 9/2008 | Heida | C07C 7/08 585/324 |
| 2013/0102822 A1 | 4/2013 | Arnold et al. | |

FOREIGN PATENT DOCUMENTS

| | | |
|---|---|---|
| JP | 2004-517952 A | 6/2004 |
| JP | 2007-520519 A | 7/2007 |
| WO | 2005/037397 A1 | 4/2005 |
| WO | 2010008109 A1 | 1/2010 |

OTHER PUBLICATIONS

Correspondence reporting an Official Letter and Search Report issued Dec. 29, 2014 in corresponding Taiwan application No. 102138064 (10 pages).
Extended European Search Report issued May 13, 2016 in corresponding European application No. 13850380.0 (4 pages).
Notification of Reasons for Refusal (Office Action) issued Jul. 12, 2016, by the Japan Patent Office in related Japanese Patent Application No. JP 2015-539656 (with English translation) (9 pages).
Second office action issued Sep. 19, 2016 in corresponding Chinese application No. 201380061757.5 (w/ translation) (17 pages).
Examination Report issued Nov. 29, 2016 in corresponding GCC application No. GC 2013-25679 (3 pages).
Office Action issued in corresponding Korean Application No. 10-2015-7013485 with English Translation dated Mar. 20, 2017 (8 pages).

* cited by examiner

BUTADIENE EXTRACTION PROCESS

CROSS-REFERENCE TO RELATED APPLICATION

This application, pursuant to 35 U.S.C. §120, claims benefit to U.S. patent application Ser. No. 14/058,637 filed Oct. 21, 2013, now U.S. Pat. No. 9,296,667, which pursuant to 35 U.S.C. §119(e), claims priority to U.S. Provisional Application Ser. No. 61/720,038, filed Oct. 30, 2012. Each of these applications is incorporated herein by reference in their entirety.

FIELD OF THE DISCLOSURE

Embodiments disclosed here relate to recovery of butadiene from a mixed hydrocarbon stream. More specifically, embodiments disclosed herein relate to an improved butadiene extraction process wherein the degasser operates at an intermediate pressure.

BACKGROUND

Butadiene is an important base chemical and is used, for example, to prepare synthetic rubbers (butadiene homopolymers, styrene-butadiene-rubber or nitrile rubber) or for preparing thermoplastic terpolymers (acrylonitrile-butadiene-styrene copolymers). Butadiene is also converted to sulfolane, chloroprene and 1,4-hexamethylenediamine (via 1,4-dichlorobutene and adiponitrile). Dimerization of butadiene also allows vinylcyclohexene to be generated, which can be dehydrogenated to form styrene.

Butadiene can be prepared from saturated hydrocarbons by refining process or by thermal cracking (steam cracking) processes, in which case naphtha is typically used as the raw material. In the course of refining or steam cracking of naphtha, a mixture of methane, ethane, ethene, acetylene, propane, propene, propyne, allene, butenes, butadiene, butynes, methylallene, $C_4$ and higher hydrocarbons are obtained.

Owing to the small differences in the relative volatilities of the components of a $C_4$ cut, obtaining 1,3-butadiene from the $C_4$ cut is a complicated distillation problem. Therefore, the separation is carried out by extractive distillation, i.e. a distillation with addition of an extractant which has a higher boiling point than the mixture to be separated and which increases the differences in the relative volatilities of the components to be separated. The use of suitable extractants allows a crude 1,3-butadiene fraction to be obtained from the $C_4$ cut mentioned by means of extractive distillation, and said fraction is subsequently further purified in purifying distillation columns.

The butadiene recovery processes typically use 3- or 4-column extractive distillation systems to separate a mixed $C_4$ stream into product fractions, including a lights/butane/butenes stream (Raffinate-1 product), a crude butadiene product, which may be sent to a conventional distillation system for further purification, and $C_3$ acetylenes (propyne) and $C_4$ acetylenes streams, which may be sent to a selective hydrogenation unit, for example.

In the present context, crude 1,3-butadiene refers to a hydrocarbon mixture which has been obtained from a $C_4$ cut from which at least 90% by weight of the sum of butanes and butenes, preferably at least 98% by weight of the sum of butanes and butenes, more preferably at least 99% by weight of the sum of butanes and butenes, and simultaneously at least 90% by weight of the $C_4$ acetylenes, preferably at least 96% by weight of the $C_4$ acetylenes, more preferably at least 99% by weight of the $C_4$ acetylenes, has been removed. Crude 1,3-butadiene contains the 1,3-butadiene product of value frequently in a proportion of at least 80% by weight, preferably 90% by weight, more preferably more than 95% by weight, remainder impurities. Accordingly, pure 1,3-butadiene refers to a hydrocarbon mixture which contains the 1,3-butadiene product of value in a proportion of at least 98% by weight, preferably of at least 99.5% by weight, more preferably in the range between 99.7 and 99.9% by weight, remainder impurities.

Typical processes to recover butadiene from mixed $C_4$ streams include extractive distillation processes, which may incorporate use of selective solvents. Examples of extractive distillation processes are found, for example, in U.S. Pat. Nos. 7,692,053, 7,393,992, 7,482,500, 7,226,527, 4,310,388, and 7,132,038, among others.

The extractive distillation processes described in the above mentioned patents typically fall into one of two categories, a conventional low pressure process including a compressor or a high pressure "compressorless" process, such as disclosed in U.S. Pat. No. 7,692,053.

The compressorless design has the advantages of lower capital costs, as this design option eliminates the recycle gas compressor entirely. However, there are several disadvantages. For example, for the compressorless design, the degasser may be operated at an overhead pressure of about 4.21 kg/cm² gage, slightly above the extractive distillation system (including the main washer, rectifier and afterwasher) pressure. Consequently, the degasser operates at correspondingly higher temperatures: about 148° C. at the top of the degasser and about 193° C. at the bottom of the degasser. In contrast, the degasser in the conventional design may be operated at an overhead pressure of only 0.7 kg/cm² gage, and at much lower temperatures: about 105° C. at the top of the degasser and about 149° C. at the bottom of the degasser.

The roughly 44° C. hotter degasser temperatures for the compressorless design results in two distinct disadvantages. First, vinyl cyclohexene (VCH, or butadiene dimer) make increases with increasing temperature and a higher dimer make results in lower yield and potentially higher equipment fouling rates. Second, there is a potential for greater risk due to having high $C_4$ acetylene concentrations at the higher operating temperatures and pressures. To mitigate this risk, the vinyl acetylene concentration in the degasser must be kept lower (below 20 mol. %). However, limiting the vinyl acetylene concentration may lead to additional 1,3-butadiene losses, and thus lower yield.

SUMMARY OF THE CLAIMED EMBODIMENTS

It has now been found that butadiene extraction processes may be operated at an intermediate pressure using a liquid ring type compressor. The use of a liquid ring compressor, among other process options presented herein, may advantageously reduce capital and operating costs, similar to the compressorless option, while mitigating the risks associated with the higher operating temperatures and pressures associated with the compressorless option. Thus, the embodiments of the processes disclosed herein encompass the best features of the conventional design (low pressure, with a compressor) with the advantages of the compressorless design (low capital and operating cost), as well as other advantages unique to the systems disclosed herein.

In one aspect, embodiments disclosed herein relate to a process for recovering 1,3-butadiene from a $C_4$ fraction. The process may include: feeding a hydrocarbon fraction containing butanes, butenes, 1,2-butadiene, 1,3-butadiene, $C_4$ acetylenes, $C_3$ acetylenes, and $C_{5+}$ hydrocarbons to an extractive distillation system; contacting the hydrocarbon fraction with a solvent in the extractive distillation system to selectively dissolve a portion of the hydrocarbon fraction; recovering a vapor fraction comprising a first portion of the butanes and the butenes from the extractive distillation system; recovering an enriched solvent fraction comprising the 1,3-butadiene, the 1,2-butadiene, $C_4$ acetylenes, $C_3$ acetylenes, $C_{5+}$ hydrocarbons, and a second portion of the butanes and the butenes; feeding the enriched solvent fraction to a rectifier to at least partially degas the enriched solvent; recovering a second portion of the butanes and butenes from the rectifier as an overheads fraction; recovering the $C_3$ and $C_4$ acetylenes, 1,3-butadiene, 1,2-butadiene, and $C_{5+}$ hydrocarbons from the rectifier as a side draw fraction; recovering a partially degassed solvent comprising 1,2-butadiene and $C_4$ acetylenes from the rectifier as a bottoms fraction; feeding at least a portion of the partially degassed solvent to a degasser to further degas the solvent; recovering an overheads fraction comprising at least one of $C_4$ acetylenes and 1,2-butadiene from the degasser; recovering a side draw fraction comprising the $C_4$ acetylenes from the degasser; recovering a bottoms fraction comprising degassed solvent from the degasser; compressing the degasser overheads fraction using a liquid ring compressor; and recycling at least a portion of the compressed degasser overheads fraction to the rectifier.

In another aspect, embodiments disclosed herein relate to a system for recovering 1,3-butadiene from a $C_4$ fraction. The system may include: a flow conduit for feeding a hydrocarbon fraction containing butanes, butenes, 1,2-butadiene, 1,3-butadiene, $C_4$ acetylenes, $C_3$ acetylenes, and $C_{5+}$ hydrocarbons to an extractive distillation system; the extractive distillation system for contacting the hydrocarbon fraction with a solvent in the extractive distillation system to selectively dissolve a portion of the hydrocarbon fraction; a flow conduit for recovering a vapor fraction comprising a first portion of the butanes and the butenes from the extractive distillation system; a flow conduit for recovering an enriched solvent fraction comprising the 1,3-butadiene, the 1,2-butadiene, $C_4$ acetylenes, $C_3$ acetylenes, $C_{5+}$ hydrocarbons, and a second portion of the butanes and the butenes; a flow conduit for feeding the enriched solvent fraction to a rectifier; the rectifier for at least partially degassing the enriched solvent; a flow conduit for recovering a second portion of the butanes and butenes from the rectifier as an overheads fraction; a flow conduit for recovering the $C_3$ and $C_4$ acetylenes, 1,3-butadiene, 1,2-butadiene, and $C_{5+}$ hydrocarbons from the rectifier as a side draw fraction; a flow conduit for recovering a partially degasses solvent comprising 1,2-butadiene and $C_4$ acetylenes from the rectifier as a bottoms fraction; a flow conduit for feeding at least a portion of the partially degassed solvent to a degasser; the degasser for further degassing the solvent; a flow conduit for recovering an overheads fraction comprising at least one of $C_4$ acetylenes and 1,2-butadiene from the degasser; a flow conduit for recovering a side draw fraction comprising the $C_4$ acetylenes from the degasser; a flow conduit for recovering a bottoms fraction comprising degassed solvent from the degasser; a liquid ring compressor for compressing the degasser overheads fraction; and a flow conduit for recycling at least a portion of the compressed degasser overheads fraction to the rectifier.

Other aspects and advantages will be apparent from the following description and the appended claims.

BRIEF DESCRIPTION OF DRAWINGS

As noted, the flow diagrams in FIGS. 1-4 are simplified, and do not illustrate pumps, valves, control valves, filters, reboilers, condensers, and other equipment commonly associated with distillation columns and general petrochemical operations, and these would be understood to be present by one skilled in the art based on the Figures and the Detailed Description provided below.

DETAILED DESCRIPTION

Embodiments disclosed here relate to recovering butadiene from mixed $C_4$ hydrocarbon streams. More specifically, embodiments disclosed herein relate to improving the operations and economics of butadiene extraction processes via use of intermediate pressures and a liquid ring type compressor.

The $C_4$ fraction to be used as starting mixture in the present processes is a mixture of hydrocarbons having predominantly four carbon atoms per molecule. $C_4$ fractions are obtained, for example, in the preparation of ethylene and/or propylene by thermal or catalytic cracking of a petroleum fraction, such as liquefied petroleum gas, light naphtha or gas oil. $C_4$ fractions may also be obtained by the catalytic dehydrogenation (oxidative and/or non-oxidative dehydrogenation) of n-butane and/or n-butene. The resulting $C_4$ fractions generally include butanes, n-butene, isobutene, 1,3-butadiene and small amounts of $C_3$ and $C_5$ hydrocarbons, including methylacetylene, as well as butynes, in particular 1-butyne (ethylacetylene) and butenyne (vinylacetylene). The 1,3-butadiene content is generally from 5 to 80% by weight. For example, a cracker or a CATADIENE unit may contain 15 to 17% butadiene, by weight. Other mixed $C_4$ feed streams may contain greater or lesser amounts of butadiene. When present in the mixed feed stream, vinylacetylene may be selectively hydrogenated to the desired 1,3-butadiene product prior to feed of the mixed $C_4$ stream to the butadiene extraction unit. In some embodiments, the mixed $C_4$ hydrocarbon stream may be provided, for example, by at least one of cracking, oxidatively dehydrogenating, and non-oxidatively dehydrogenating a $C_4$ hydrocarbon stream comprising butane in one or more dehydrogenation reactors to produce a product gas stream comprising butane, butene, and butadiene.

The above-described hydrocarbon fraction, containing butanes, butenes, 1,2-butadiene, 1,3-butadiene, $C_4$ acetylenes, $C_3$ acetylenes, and $C_{5+}$ hydrocarbons, is fed to a butadiene extraction unit for separation and recovery of the various hydrocarbons, including one or more lights/butanes/butenes fractions (commonly referred to as a Raffinate-1 product), a 1,3-butadiene fraction, a $C_3$ acetylenes (propyne) fraction, a $C_4$ acetylenes fraction, which may include a portion of the 1,2-butadiene, and a heavies fraction, which may include a portion of the 1,2-butadiene and the $C_{5+}$ hydrocarbons. In some embodiments, dimers of butadiene may be formed upstream of the butadiene extraction unit or during processing of the hydrocarbon fraction within the butadiene extraction unit. The vinylcyclohexene components may be recovered with the heavies fraction, or may be recovered as a separate fraction containing vinylcyclohexene.

Figure 1:
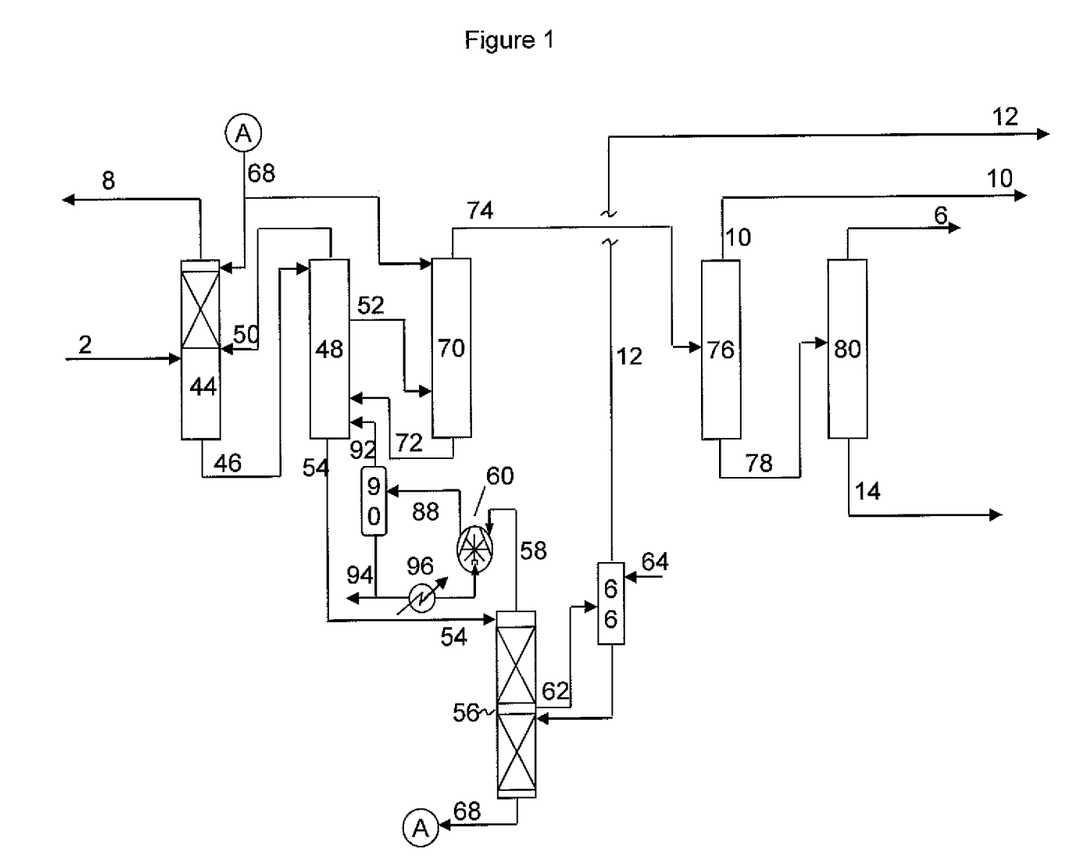
FIG. 1 is a simplified flow diagram of a process for butadiene recovery according to embodiments disclosed herein.

It has been found that butadiene extraction processes may be improved via use of a liquid ring type compressor for compressing at least a portion of the overheads from the degasser. Referring now to FIG. 1, a simplified process flow diagram for recovering butadiene according to embodiments disclosed herein is illustrated. A mixed hydrocarbon feed 2, including hydrocarbons such as butanes, butenes, 1,2-butadiene, 1,3-butadiene, methyl acetylene, vinyl acetylene, and $C_5+$ hydrocarbons, may be fed to a feed vaporization system (not shown) to vaporize the mixed hydrocarbon feed. The vaporized feed is then fed to main wash column 44. In main wash column 44, the vaporized feed is contacted with a solvent, and the butanes and butenes are separated from the more soluble 1,3-butadiene, 1,2-butadiene, methyl acetylene, vinyl acetylene, and $C_{5+}$ hydrocarbons.

Solvents useful in the process as illustrated in FIG. 1 may include butyrolactone, nitriles such as acetonitrile, propionitrile, methoxypropionitrile, ketones such as acetone, furfural, N-alkyl-substituted lower aliphatic amides such as dimethylformamide, diethylformamide, dimethylacetamide, diethylacetamide, N-formylmorpholine, N-alkyl-substituted cyclic amides (lactams) such as N-alkylpyrrolidones, especially N-methylpyrrolidone (NMP). In some embodiments, alkyl-substituted lower aliphatic amides or N-alkyl-substituted cyclic amides, dimethylformamide, acetonitrile, furfural or NMP are used.

In some embodiments, it is also possible to use mixtures of these extractants with one another, for example of NMP and acetonitrile, mixtures of these extractants with cosolvents and/or tert-butyl ethers, e.g. methyl tert-butyl ether, ethyl Cert-butyl ether, propyl tert-butyl ether, n- or isobutyl tert-butyl ether. In other embodiments, NMP may be in aqueous solution, with from 0 to about 20 weight % water, or with from 7 to 10 weight % water, or with 8 to 8.5 weight % water in other embodiments.

The butanes and butenes are recovered from main wash column 44 as an overheads fraction 8 (Raffinate 1). The enriched solvent, including the dissolved hydrocarbons, is recovered from main wash column 44 as a bottoms fraction 46.

Bottoms fraction 46 is then fed to rectifier 48 to at least partially degas the enriched solvent. Any dissolved butanes and butenes, as well as other light components may be recovered from rectifier 48 as an overheads fraction 50, which may recycled for re-processing in main wash column 44. Methyl acetylene and butadienes, including both 1,2-butadiene and 1,3-butadiene, and $C_{5+}$ hydrocarbons may be recovered from rectifier 48 as a side draw 52, and a degassed solvent, which may contain various $C_4$ components including 1,2-butadiene, 1-butyne, and vinyl acetylene, may be recovered from rectifier 48 as a bottoms fraction 54.

Bottoms fraction 54 may be fed to a degasser 56, for separation of the solvent, entrained $C_4$ components, and a $C_4$ acetylene fraction, which may also include 1,2-butadiene.

The $C_4$ vapors may be recovered from degasser and cooling column 56 as an overheads fraction 58, which may be compressed via liquid ring compressor 60.

Liquid ring compressor 60 serves two functions: compression of the degasser overhead fraction and cooling of the compressed gas before recycle to the rectifier 48. Following compression, a portion of the compressed gases may be recycled to rectifier 48. In some embodiments, the compressed degasser overhead fraction may be recovered via flow line 88 and fed to a separator 90 to separate any condensed gases. The vapor fraction recovered from separator 90 may then be recycled via flow line 92 to rectifier 48. The condensate fraction may be recovered from separator 90 via flow line 94, at least a portion of which may be cooled via heat exchanger 96 and recycled to liquid ring compressor 60.

A vinyl acetylene fraction may be withdrawn from degasser 56 as a side draw fraction 62, washed with water fed via line 64 in acetylene washer 66, and recovered as vinyl acetylene fraction 12. The degassed solvent may be recovered from degasser 56 as a bottoms fraction 68 for recycle and feed to main wash column 44 and afterwash column 70, where the hydrocarbons in the side draw fraction 52 may be separated from the solvent. Solvent may be recovered from afterwash column 70 as a bottoms fraction 72 and recycled to rectifier 48, and a crude butadiene product stream may be recovered from afterwash column 70 as an overheads fraction 74.

The crude butadiene product (overheads fraction 74) leaves the extractive distillation section and is then fed to a methyl acetylene distillation column 76, where methyl acetylene is recovered as an overheads fraction 10. The bottoms fraction 78 contains the 1,3-butadiene, 1,2-butadiene, and heavier hydrocarbons, and is fed to butadiene fractionator 80. 1,3-Butadiene having a purity of greater than 99.6% is recovered from butadiene column 80 as an overheads fraction 6, and the 1,2-butadiene and heavies are recovered as a bottoms fraction 14.

In some embodiments, it may be desired to hydrogenate acetylenes in fractions 10, 12 to produce additional olefins and dienes. Additionally or alternatively, it may be desired to use a green oil column to recover oligomers of butadiene (vinyl cyclohexane) and oligomers of other olefinic components in the hydrocarbon feed stream that may be produced during the separations noted above.

Figure 2:
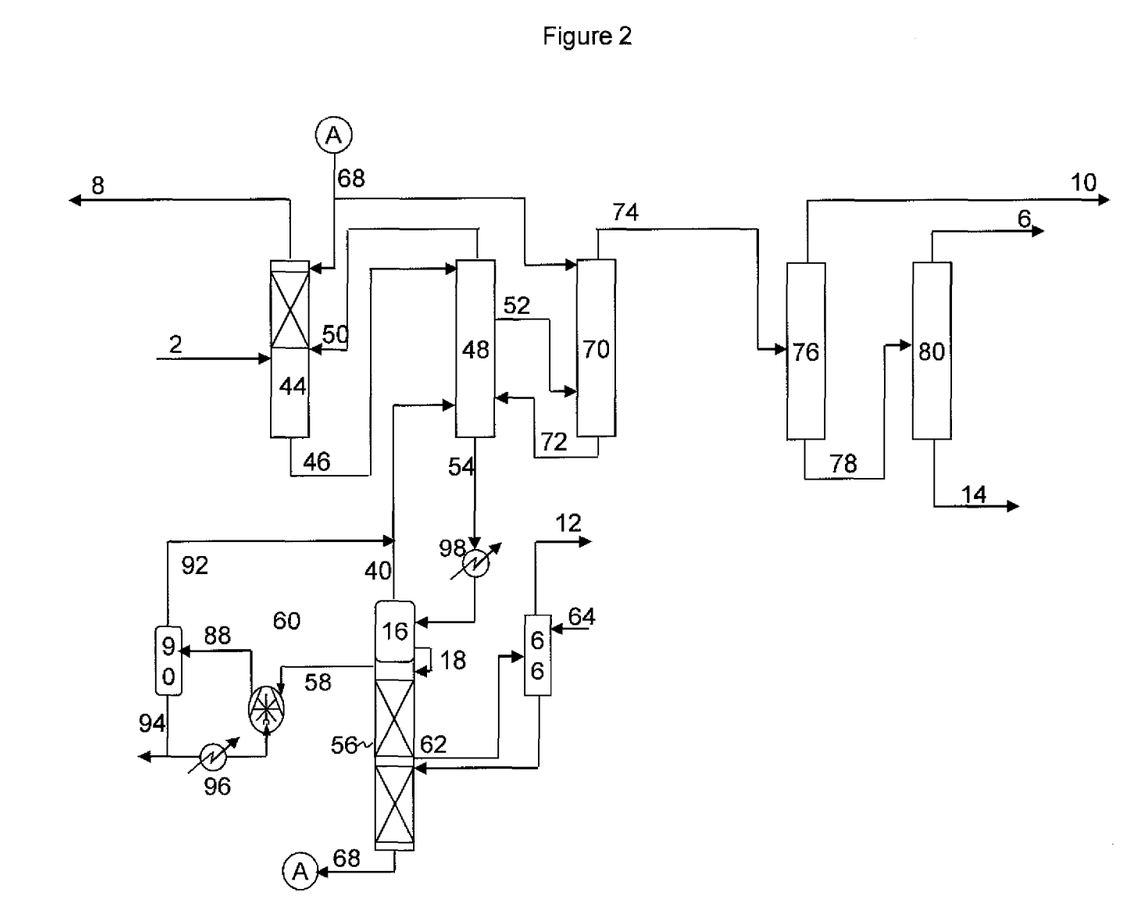
FIG. 2 is a simplified flow diagram of a process for butadiene recovery according to embodiments disclosed herein.

Referring now to FIG. 2, a simplified flow diagram for a process for recovering 1,3-butadiene according to embodiments disclosed herein is illustrated, where like numerals represent like parts. In this embodiment, the bottoms fraction recovered from the rectifier 48 via flow stream 54 may be heated via indirect heat exchange prior to feed to the degasser 56, such as via heat exchanger 98. The heating of the rectifier bottoms may vaporize a portion of the remaining dissolved gasses, such as 1,2-butadiene or $C_4$ acetylenes. Prior to feeding of the heated rectifier bottoms to the degasser, the heated bottoms may be fed to a degasser feed drum 16 to phase separate the vaporized portion from the liquid portion of the effluent recovered from heater 98. A liquid phase may then be recovered from feed drum 16 and fed via flow line 18 to degasser 56 and processed as described above with respect to FIG. 1. The vapor phase recovered from feed drum 16 via flow line 40 may then be combined with the compressed vapor fraction of flow line 92 for recycle to rectifier 48.

Degasser feed drum 16 may operate at a pressure slightly above the rectifier 48 bottoms pressure, allowing the vapor phase recovered from feed drum 16 to flow freely back to rectifier 48 without the need for vapor recompression. Some of the heat input added via exchanger 98 is thus returned to rectifier 48 in the form of the flashed vapors. The recycle of gas from drum 16 to rectifier 48 at a slightly elevated temperature may thus add heat to rectifier 48, and may result in additional pre-degassing in the bottom section of rectifier 48, contributing to an overall lower degassing requirement in degasser 56.

Degasser feed drum 16 may be a separate vessel, or as illustrated, may be integral with the degasser 56, forming a single vessel structure. Integrating the feed drum and the degasser into a single vessel may reduce capital costs. By locating feed drum 16 above or on top of degasser 56, the liquid phase in the feed drum may easily flow into the top of the degasser without the need for additional pumps. Part of the heat input from exchanger 98 thus also flows to degasser 56 in the form of sensible heat contained in the un-flashed liquid fed to degasser 56 via flow line 18.

Overall, the use of exchanger 98 and phase separation in drum 16 may provide for two stages of flashing, in feed drum 16 and degasser 56, where feed drum 16 may be operated at a pressure greater than that of degasser 56. Use of the two stage separations may result in more efficient C4 degassing, improving separations of the C4 hydrocarbons from the solvent. Further, dissolved gases degassed in feed drum 16 and recovered via flow line 40 are at a higher pressure level, and do not require recompression for recycle to rectifier 48.

Degasser 56 may be operated at a pressure lower than rectifier 56, but only the gases recovered via flow line 58 require recompression. As a result, liquid ring compressor 60 may be sized to account for the reduced vapor flow and reduced compression requirements, resulting in lower capital and operating expenses. For example, in some embodiments, a ratio of the vapor flow rate of the compressed degasser overheads (stream 92) to the vapor flow rate of the vapor phase recovered from degasser feed drum 16 (stream 40) may be in the range from about 0.1:1 to about 1:1; in the range from about 0.2:1 to about 0.8:1 in other embodiments; and from about 0.25:1 to about 0.5:1 in yet other embodiments.

Figure 3:
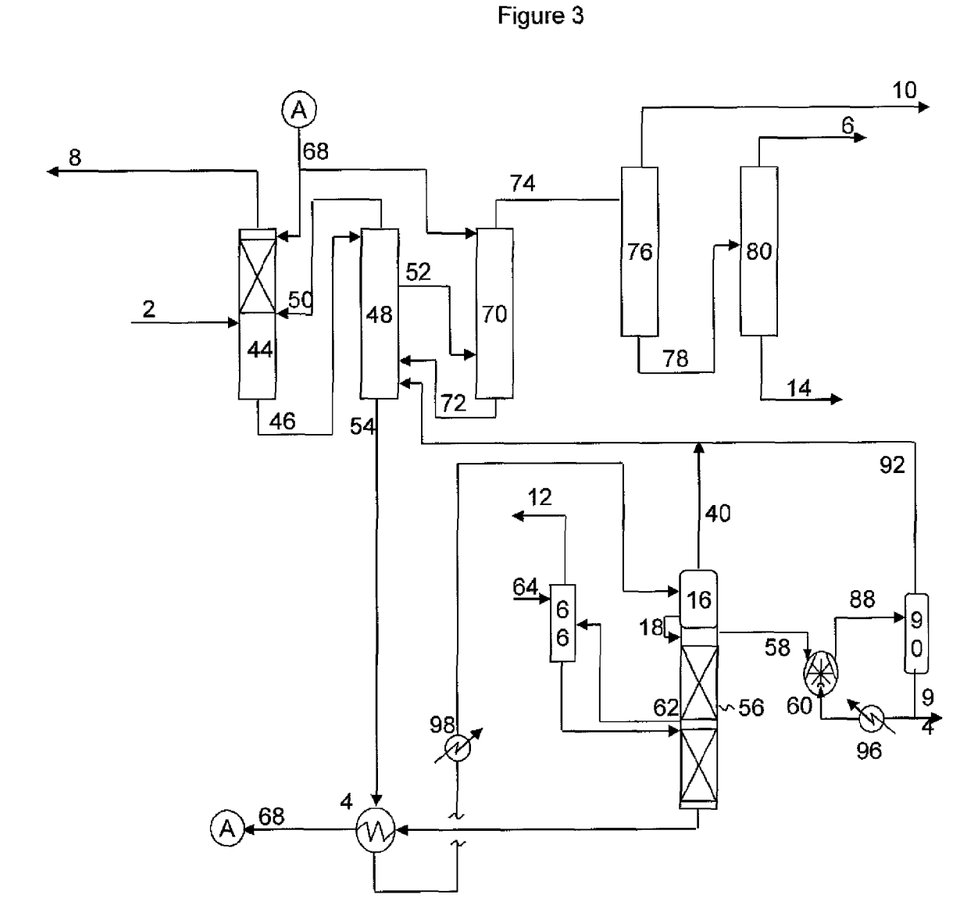
FIG. 3 is a simplified flow diagram of a process for butadiene recovery according to embodiments disclosed herein.

Referring now to FIG. 3, a simplified flow diagram for a process for recovering 1,3-butadiene according to embodiments disclosed herein is illustrated, where numerals represent like parts. In this embodiment, the bottoms fraction recovered from the rectifier 48 via flow stream 54 may be heated via indirect heat exchange prior to feed to the degasser 56, such as via heat exchangers 4, 98, to vaporize a portion of the remaining dissolved gasses, such as 1,2-butadiene or $C_4$ acetylenes. Heat exchanger 4 may be used to recover heat from the bottoms fraction 68 recovered from degasser 56. Heat exchanger 98 may then be used further heat the rectifier bottoms before processing of the partially vaporized rectifier bottoms in degasser feed drum 16 and processed as described above with respect to FIG. 2.

Figure 4:
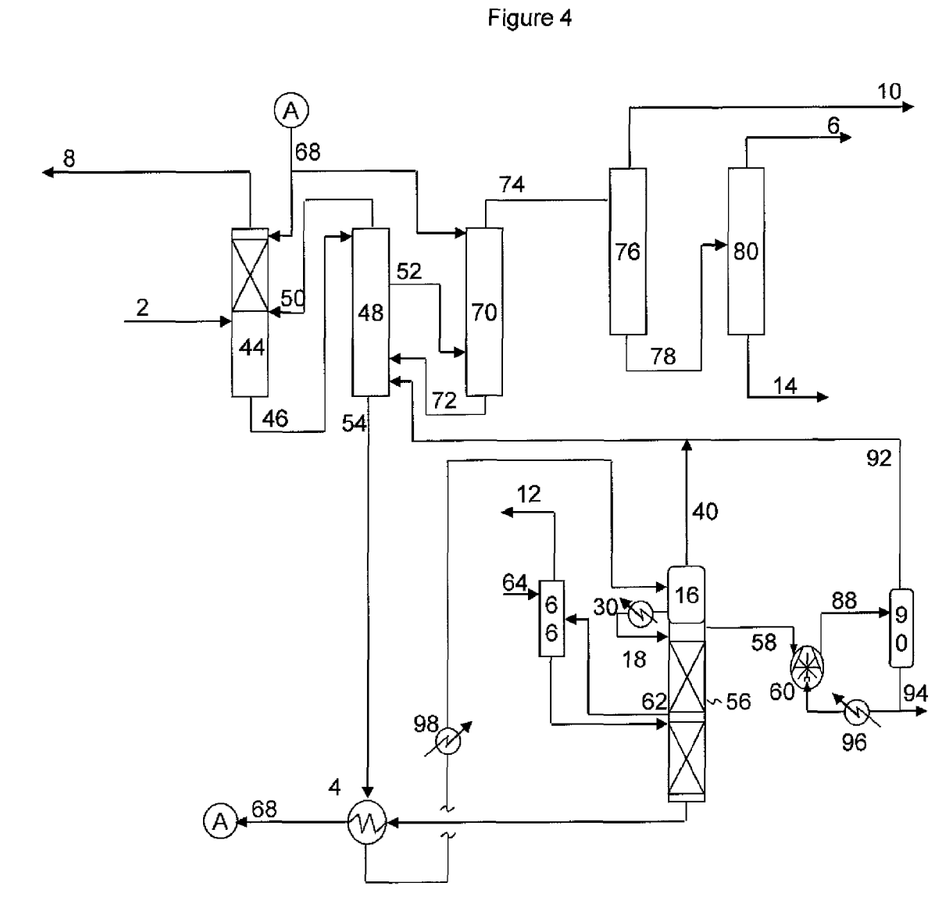
FIG. 4 is a simplified flow diagram of a process for butadiene recovery according to embodiments disclosed herein.

Referring now to FIG. 4, a simplified flow diagram for a process for recovering 1,3-butadiene according to embodiments disclosed herein is illustrated, where like numerals represent like parts. In this embodiment, the liquid portion recovered from degasser feed drum 16 via flow line 18 is heated via indirect heat exchange in heat exchanger 30 to provide addition heat to the degasser feed, which is then processed as described above.

As discussed above with respect to FIGS. 2-4, the rectifier bottoms may be heated via indirect heat exchange using exchangers 4, 98. In some embodiments, exchanger 98 may use a heat exchange medium, such as water, steam, or a synthetic organic heat transfer fluid, such as DOWTHERM or others as may be known to those in the art. It may also be desirable to suppress vaporization in the heat exchangers and associated piping, favoring vaporization in feed drum 16 or degasser 56 to minimize or prevent fouling. Thus, in some embodiments, heat exchangers 4, 98 may be suppressed vaporization heaters.

Degasser feed drum 16 may be operated at a pressure in the range from about 3.5 kg/cm$^2$ gage to about 5.5 kg/cm$^2$ gage in some embodiments; in the range from about 4 kg/cm$^2$ gage to about 5 kg/cm$^2$ gage in other embodiments; and from about 4.25 kg/cm$^2$ gage to about 4.75 kg/cm$^2$ gage in yet other embodiments, such as about 4.5 kg/cm$^2$ gage. Degasser feed drum 16 may be operated at a temperature in the range from about 110° C. to about 150° C. in some embodiments; in the range from about 120° C. to about 140° C. in other embodiments; and in the range from about 125° C. to about 135° C. in yet other embodiments, such as about 130° C.

Degasser 56 may be operated at a pressure in the range from about 1.5 kg/cm$^2$ gage to about 3.5 kg/cm$^2$ gage in some embodiments; in the range from about 2 kg/cm$^2$ gage to about 3 kg/cm$^2$ gage in other embodiments; and from about 2.25 kg/cm$^2$ gage to about 2.75 kg/cm$^2$ gage in yet other embodiments, such as in the range from about 2.3 kg/cm$^2$ gage to about 2.5 kg/cm$^2$ gage. Degasser 56 may be operated at an overhead temperature in the range from about 100° C. to about 150° C. in some embodiments; in the range from about 110° C. to about 140° C. in other embodiments; and in the range from about 120° C. to about 130° C. in yet other embodiments, such as about 125° C. Degasser 56 may be operated at a bottoms temperature in the range from about 150° C. to about 200° C. in some embodiments; in the range from about 160° C. to about 190° C. in other embodiments; and in the range from about 170° C. to about 180° C. in yet other embodiments, such as about 175° C.

Rectifier 48 may be operated at a pressure in the range from about 3 kg/cm$^2$ gage to about 5 kg/cm$^2$ gage in some embodiments; in the range from about 3.5 kg/cm$^2$ gage to about 4.5 kg/cm$^2$ gage in other embodiments; and from about 4 kg/cm$^2$ gage to about 4.5 kg/cm$^2$ gage in yet other embodiments, such as in the range from about 4.1 kg/cm$^2$ gage to about 4.2 kg/cm$^2$ gage. Rectifier 48 may be operated at an overhead temperature in the range from about 40° C. to about 90° C. in some embodiments; in the range from about 50° C. to about 80° C. in other embodiments; and in the range from about 60° C. to about 70° C. in yet other embodiments, such as in the range from about 63 to about 68° C. Rectifier 48 may be operated at a bottoms temperature in the range from about 60° C. to about 120° C. in some embodiments; in the range from about 70° C. to about 110° C. in other embodiments; and in the range from about 75° C. to about 100° C. in yet other embodiments, such as in the range from about 80° C. to about 95° C.

Heat may be supplied to the rectifier via indirect heat exchange in a reboiler using a heating medium having a temperature of less than 130° C. For example, the heating medium used to heat the rectifier reboiler may have an operating temperature in the range from about 80° C. to about 130° C. in some embodiments; in the range from about 90° C. to about 125° C. in other embodiments; and in the range from about 100° C. to about 120° C. in yet other embodiments. In some embodiments, the heat exchange medium used in the rectifier reboiler may be controlled such that the process-side temperature increase across the reboiler is in the range from about 5° C. to about 15° C.; and in the range from about 8° C. to about 12° C. in other embodiments, such as a delta of about 10° C.

The two-stage degassing provided for in the degasser feed drum 16 and the degasser 56, as well as heat introduced to rectifier 56 via vapor streams 40, 92 may allow the rectifier reboiler to operate at a low percent vaporization. For example, in some embodiments, the rectifier reboiler may operate having a percent vaporization across the reboiler in the range from about 3 wt. % to about 9 wt. %; in the range from about 4 wt. % to about 8 wt. % in other embodiments; and in the range from about 5 wt. % to about 7 wt. % in yet other embodiments, such as in the range from about 6 wt. % to about 6.5 wt%. The combination of low percent vaporization and low temperatures (both hot side and cold side) may significantly reduce fouling in the rectifier reboiler. Additionally, the low percent vaporization and reduced fouling may permit the rectifier reboiler to be a conventional type heat exchanger, including single-pass heat exchangers, as opposed to a suppressed vaporization type exchanger.

EXAMPLE

A process for recovering butadiene according to embodiments disclosed herein, similar to that illustrated in FIG. 3, is compared to a conventional process for recovering butadiene (using a screw type or centrifugal compressor as well as a cooling column) and a compressorless process (also including a cooling column) for recovering butadiene, using the following conditions.

For the compressorless design, the degasser is operated at an overhead pressure of 4.21 kg/cm$^2$ gage, slightly above the extractive distillation system (main washer, rectifier and afterwasher) pressure. Consequently, the degasser operates at correspondingly higher temperatures: 148° C. at top and 193° C. at bottom.

For the conventional process, the degasser operates at an overhead pressure of only 0.7 kg/cm$^2$ gage, and at much lower temperatures: 105° C. at top and 149° C. at bottom.

For this example, the embodiment as illustrated in FIG. 3 uses a once-through, co-current rectifier reboiler that uses partially cooled degasser bottoms (lean solvent) on the shell side. Partial vaporization (degassing) occurs in the reboiler tubes, and the vapor/liquid mixture is heated to 90° C. The partially degassed rich solvent at 90° C. is then pumped by a degasser feed pump to subsequent exchangers where it is further heated in suppressed vaporization type exchangers. The degasser feed pump provides sufficient discharge pressure to ensure that no vaporization (degassing) occurs in any of the exchangers. The first exchanger is the tube side of the degasser feed/effluent exchanger, where the rich solvent is heated up to approximately 138° C. on the tube side. The degasser feed/effluent exchanger is a two shell exchanger because of the large temperature cross that occurs in this exchanger. Degasser bottoms (lean solvent) at 175° C. are used as the heating medium on the shell side of the exchanger. The lean solvent is cooled to 120° C. in the degasser feed/effluent exchanger before being sent to the shell side of the rectifier reboiler and subsequently to the butadiene column reboiler, feed vaporizer, and solvent cooler.

Heated rich solvent from the degasser feed/effluent exchanger is then sent to the degasser feed heater where the rich solvent is further heated against low pressure steam (150° C.) to a temperature of approximately 138° C. Rich solvent at its final temperature is then flashed across a control valve into the degasser feed drum, which sits on top of the degasser. The feed drum rides off of the rectifier bottoms pressure, and the flashed gas flows freely back to the rectifier where it enters below the bottom bed. Unflashed liquid from the degasser feed drum then flows by pressure difference/gravity into the top of the degasser where additional feed flashing occurs. The partially degassed solvent then flows down the multi-bed degasser, where essentially all of the remaining $C_4$ hydrocarbons are completely stripped from the solvent. Stripping heat is provided by the Degasser reboiler, utilizing medium pressure steam. The degasser also serves to concentrate the $C_4$ acetylenes (vinyl- and ethy-acetylene), 1,2-butadiene and VCH. These components are removed at their point of highest concentration via a liquid side draw.

A comparison of flow rates and energy requirements for these processes is presented in Table 1.

TABLE 1

| | Example 1 | | | Conventional | | | Compressorless | | |
|---|---|---|---|---|---|---|---|---|---|
| Unit Operation | Degassing kg/h | Duty mm kcal/h | Temp. ° C. | Degassing kg/h | Duty mm kcal/h | Temp. ° C. | Degassing kg/h | Duty mm kcal/h | Temp. ° C. |
| Rectifier Reboiler | 21797 | 4.361 | 90 | 39918 | 9.588 | 120/103.8 | 27834 | 7.917 | 120/108 |
| Degasser Feed | 26429 | 9.678 | 137.9/129 | — | — | — | — | — | — |
| Flash Drum | 26429 | 0.725 | | — | — | — | — | — | — |
| Degasser Inlet Flash | 6326 | — | 129/124.6 | 22101 | 1.163 | 120/104.5 | 16980 | 9.861 + 0.730 | 160/147 |
| Degasser | 9945 | 10.757 | 175 | 6793 | 9.168 | 150 | 9835 | 11.053 | 193 |
| Total | 64498 | 25.521 | | 68812 | 19.919 | | 54.649 | 29.561 | |
| Solvent Flow (kg/h) | 290082 | | | 311433 | | | 316012 | | |
| Compressor Flow (kg/h) | 18703 | | | 31256 | | | — | | |
| Compression Ratio | 1.61 | | | 3.42 | | | — | | |
| Power (kw) | 292.6 | | | 799.2 | | | — | | |
| Rich Solvent Dissolved Gas (kg/h) | 64475 | | | 68783 | | | 54650 | | |

As shown by the table above, for the process of Example 1, process heat (degasser bottoms) is advantageously exchanged for high pressure degassing (rectifier bottoms) and advantageously exchanged for low pressure degassing (degasser feed). Process heat is added to the rectifier bottoms (high pressure level) in two steps vs. the one-step heat addition in the conventional design. The first step is a "mild" heat input via the Rectifier reboiler, which is a once-thru reboiler that heats the rich solvent from 80° C. to 90° C. (only 10° C. delta T). At this low outlet temperature, a suppressed-vaporization reboiler is not required, thus no rectifier bottoms pump is required. Even though conditions are mild, one-third of the dissolved gases are removed from the rich solvent in this first degassing step. The percent vaporization in the rectifier reboiler is also quite low (6.2 wt. %). The heating medium inlet temperature on the hot side of the rectifier reboiler is controlled at 120° C., which is significantly below the 150° C. heating medium used in the conventional design. The combination of low temperatures (both hot side and cold side) and the low percent vaporization avoids the issue of fouling in the rectifier reboiler.

Figure 5:
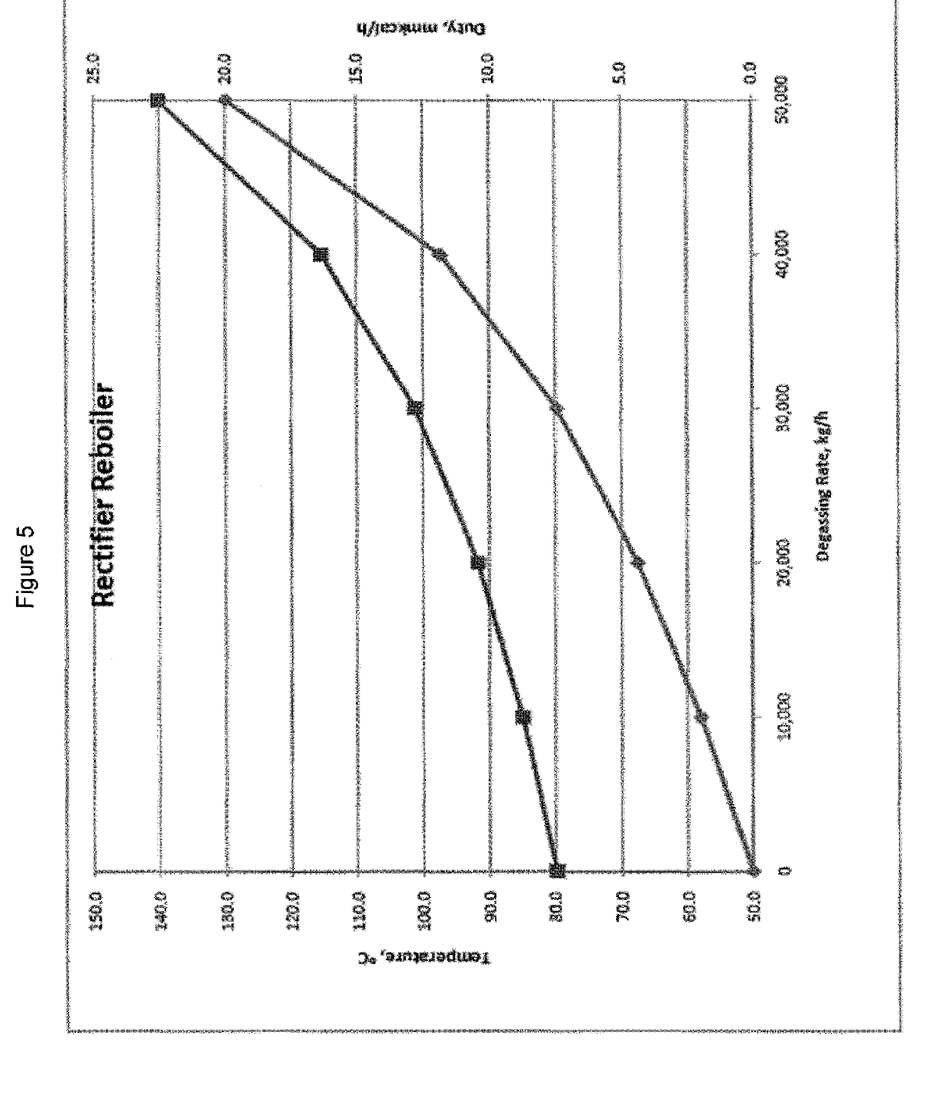
FIG. 5 is a comparison of vaporization percentages versus reboiler duty as a function of temperature for two different pressures.

In contrast, the conventional design heats up the rectifier bottoms from 76° C. to 120° C. (44° C. delta T) in the first degassing step. The process of Example 1 achieves almost half of the degassing as in the conventional design, with only a 10° C. temperature rise vs. the 44° C. temperature rise of the conventional design. Thus, there are clearly diminishing returns when trying to accomplish the high pressure degassing in a single step, as shown in FIG. 5.

The second step is a more "severe" heat input via the degasser feed/effluent exchanger, which requires a suppressed-vaporization reboiler (similar to the conventional design). In the process of Example 1, the rich solvent is heated to about 140° C. in a suppressed vaporization heater, the degasser feed/effluent exchanger, and flashed into the feed drum located at the top of (and part of) the degasser. The drum operates at a pressure slightly above the rectifier bottoms pressure, so the vapor flows freely back to the rectifier bottoms without the need for vapor recompression. The high level heat input is in the form of the flashed vapor returned to the rectifier. The un-flashed liquid then flows by pressure differential and gravity to the top of the degasser, where additional flashing occurs.

The two-step high pressure degassing is also more efficient in terms of $C_4$ degassing. Two stages of flashing provide better separation of $C_4$s from the solvent. In other words, more $C_4$s and less solvent are vaporized compared to the conventional design.

Because of the higher operating pressure of the degasser, recycle gas is returned to the Rectifier at a slightly higher temperature than in the conventional design and more "pre-degassing" occurs in the bottom section of the rectifier. This contributes to an overall lower degassing requirement.

Process heat is added to the degasser feed (low pressure degassing) by means of the sensible heat contained in the un-flashed liquid in the degasser feed drum. In other words, part of the heat input from the degasser feed/effluent exchanger ends up in the feed to the degasser.

Because almost 75% of the dissolved gases in the rich solvent are degassed at the higher pressure level (not requiring recompression) vs. only 58% in the conventional design, the capacity of the liquid ring compressor of Example I is only 60% of the capacity of the screw-type compressor required for the conventional design. The degasser operates at a pressure slightly less than 2 kg/cm$^2$ below the rectifier pressure. Consequently, the compression ratio required between the degasser and the rectifier is only 1.61 vs. 3.42 for the conventional design. The combination of lower flow and lower compression ratio allows the use of a liquid ring compressor instead of the more-expensive centrifugal or screw-type compressor employed in the conventional design. The smaller size (flow and compression ratio) of the liquid ring compressor makes it even less expensive.

The combination of lower flow and lower compression ratio results in a power consumption that is only 37% of the power required in the conventional design, even after accounting for the expected lower adiabatic efficiency of the liquid ring compressor (50% vs. 76%).

The cooling column used in the conventional design is eliminated in the process of Example 1, and its function is largely replaced by the liquid ring compressor. Thus, the liquid ring compressor accomplishes two operations: compressing the degasser overhead; and cooling the compressed gas.

As noted above, in some embodiments, a second degasser feed heater can be added at the bottoms of the degasser feed drum to provide some additional low-level utility heat to the degasser feed. In this case, the heater could be located at grade and the liquid static head at the inlet to the exchanger would be used to suppress vaporization. The low pressure steam utilized would displace an equivalent amount of medium pressure steam, resulting in better economics. This option may also depend on project specific availability of low pressure steam and relative utility costs.

The combined degasser feed drum/degasser design has no significant cost penalty.

For example, the degasser feed/effluent exchanger is a suppressed vaporization reboiler, there is already sufficient fluid pressure to overcome the static head to feed into the drum located at the higher elevation. In the conventional design this is simply chewed up across the control valve. Thus, there is no extra cost associated with pumping into the drum mounted on top of the degasser. Additionally, the degasser is designed to be liquid-filled during chemical cleaning and passivation. The addition of a drum on the top of the degasser does not add significantly to the cost of the tower. Furthermore, until just recently, all previous degasser designs had the acetylene washer mounted on the side of the degasser. The acetylene washer is significantly bigger and heavier than the feed drum, and it was installed in an asymmetric position. There is little or no extra cost associated with mounting the drum on top of the degasser. Further, the cost of the drum on top of the tower is less than for a stand-alone drum: only one additional head is required; the incremental cost for additional shell length is small; there is no additional piece count; and no additional plot area is required.

The degasser operates at a higher pressure and temperature than the degasser in the conventional design. Although the bottoms temperature (175° C.) is higher than the conventional design (150° C.), it is significantly lower than the degasser bottoms temperature in the compressorless design (193° C.). Thus, the process of Example 1 benefits from the pre-degassing in the bottom of the rectifier and the degassing and compression area.

Compared to the conventional butadiene extraction design, embodiments disclosed herein may have one or more of the following advantages. 1. Operation of the degasser at a higher pressure and temperature. 2. Replacement of the conventional recycle gas compressor (centrifugal or screw-type) with a smaller, less-expensive liquid ring compressor. 3. Replacement of the conventional solvent exchangers (3-shell design) with the following: a. rectifier reboiler (1 shell) b. degasser feed/effluent exchanger (2 shells). 4. Use of a feed flash drum mounted on top of the degasser. This allows the recovery of flashed vapor without the need for recompression and also eliminates the need for a second set of pumps between the rectifier and the degasser (see item 4). 5. Elimination of the rectifier bottoms pumps (high capacity/high head). 6. Elimination of cooling column (cooling provided in the liquid ring compressor). 7. Elimination of the cooling column bottoms pumps (coolant flow is small and by pressure letdown). 8. Smaller solvent and water cooler (only 1 shell). 9. Lower equipment cost. 10. Lower operating cost.

Compared to the Compressorless butadiene extraction design, embodiments disclosed herein may have one or more of the following advantages. 1. Operation of the degasser at a lower pressure and temperature. 2. Replacement of the solvent exchangers (3-shell design) with a smaller rectifier reboiler (1-shell design). 3. Smaller degasser feed/effluent exchanger. 4. Addition of a small, low-cost liquid ring compressor, cooler and knock-out drum. 5. Addition of a feed flash drum mounted on top of the degasser. 6. elimination of the rectifier bottoms pumps (high capacity/high head). 7. Significantly less risk: degasser bottoms temperature is 175° C. vs. 193° C. for compressorless option, resulting in less fouling and a higher limit on inlet $C_4$ acetylenes concentration. 8. Higher yield: degasser bottoms temperature is 175° C. vs. 193° C. for compressorless option, resulting in less fouling and a higher limit on inlet $C_4$ acetylenes concentration. 9. Expected lower equipment cost. 10. Expected lower operating cost.

As shown above, butadiene extraction processes according to embodiments disclosed herein may be operated at a relative intermediate pressure using a liquid ring type compressor. The use of a liquid ring compressor, among other process options presented herein, may advantageously reduce capital and operating costs, similar to the compressorless option, while mitigating the risks associated with the higher operating temperatures and pressures of the compressorless option. Thus, the embodiments disclosed herein encompass the best features of the conventional design (low pressure, with a compressor) with the advantages of the compressorless design (low capital and operating cost), as well as other advantages unique to the systems disclosed herein.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:

1. A system for recovering 1,3-butadiene from a $C_4$ fraction, comprising:
   a flow conduit for feeding a hydrocarbon fraction containing butanes, butenes, 1,2-butadiene, 1,3-butadiene, $C_4$ acetylenes, $C_3$ acetylenes, and $C_{5+}$ hydrocarbons to an extractive distillation system;
   the extractive distillation system for contacting the hydrocarbon fraction with a solvent in the extractive distillation system to selectively dissolve a portion of the hydrocarbon fraction;
   a flow conduit for recovering a vapor fraction comprising a first portion of the butanes and the butenes from the extractive distillation system;
   a flow conduit for recovering an enriched solvent fraction comprising the 1,3-butadiene, the 1,2-butadiene, $C_4$ acetylenes, $C_3$ acetylenes, $C_{5+}$ hydrocarbons, and a second portion of the butanes and the butenes;
   a flow conduit for feeding the enriched solvent fraction to a rectifier;
   the rectifier for at least partially degassing the enriched solvent;
   a flow conduit for recovering a second portion of the butanes and butenes from the rectifier as an overheads fraction;
   a flow conduit for recovering the $C_3$ and $C_4$ acetylenes, 1,3-butadiene, 1,2-butadiene, and $C_{5+}$ hydrocarbons from the rectifier as a side draw fraction;
   a flow conduit for recovering a partially degassed solvent comprising 1,2-butadiene and $C_4$ acetylenes from the rectifier as a bottoms fraction;
   a flow conduit for feeding at least a portion of the partially degassed solvent to a degasser;
   the degasser for further degassing the solvent;
   a flow conduit for recovering an overheads fraction comprising at least one of $C_4$ acetylenes and 1,2-butadiene from the degasser;
   a flow conduit for recovering a side draw fraction comprising the $C_4$ acetylenes from the degasser;
   a flow conduit for recovering a bottoms fraction comprising degassed solvent from the degasser;
   a liquid ring compressor for compressing the degasser overheads fraction; and
   a flow conduit for recycling at least a portion of the compressed degasser overheads fraction to the rectifier.

2. The system of claim 1, further comprising:
   a separator for phase separating the compressed degasser overheads fraction to recover a condensate fraction; and
   a flow conduit for recycling at least a portion of the condensate fraction to the liquid ring compressor.

3. The system of claim 1, further comprising:
   a heat exchanger for heating the partially degassed solvent via indirect heat exchange to vaporize at least a portion of the dissolved 1,2-butadiene and/or $C_4$ acetylenes;
   a flow conduit for feeding the heated partially degassed solvent to a degasser feed drum;
   the degasser feed drum for phase separating the vaporized portion of the 1,2-butadiene and/or $C_4$ acetylenes from the heated partially degassed solvent;
   a flow conduit for recovering a vapor phase from the degasser feed drum comprising at least one of 1,2-butadiene and C4 acetylenes;
   a flow conduit for recovering a liquid phase from the degasser feed drum and feeding of the liquid phase from the degasser feed drum to the degasser as the at least a portion of the partially degassed solvent.

4. The system of claim 3, further comprising a mixing device for admixing the vapor phase recovered from the degasser feed drum and the at least a portion of the compressed degasser overheads and recycling the combined portion to the rectifier.

5. The system of claim 3, wherein the heat exchanger for heating the partially degassed solvent via indirect heat exchange comprises at least one of:
   a heat exchanger for contacting the partially degassed solvent with the degasser bottoms fraction via indirect heat exchange; and
   a heat exchanger for contacting the partially degassed solvent with a heat exchange medium comprising at least one of oil, water, and steam.

6. The system of claim 5, wherein the heat exchanger(s) for contacting the partially degassed solvent comprise a suppressed vaporization heater.

7. The system of claim 1, further comprising a reboiler to supply heat to the rectifier via indirect heat exchange, wherein the reboiler comprises a single pass heat exchanger.

8. A system for recovering 1,3-butadiene from a $C_4$ fraction, comprising:
- an extractive distillation system for contacting a hydrocarbon fraction containing butanes, butenes, 1,2-butadiene, 1,3-butadiene, $C_4$ acetylenes, $C_3$ acetylenes, and $C_{5+}$ hydrocarbons with a solvent to produce a vapor fraction and an enriched solvent fraction;
- a rectifier for at least partially degassing the enriched solvent fraction and producing (i) a rectifier overheads fraction, (ii) a rectifier side draw fraction, and (iii) a rectifier bottoms fraction;
- a degasser for further degassing the rectifier bottoms fraction and producing (i) a degasser overheads fraction, (ii) a degasser side draw fraction; and (iii) a degasser bottoms fraction;
- a liquid ring compressor for compressing the degasser overheads fraction; and
- a flow conduit for recycling at least a portion of the compressed degasser overheads fraction to the rectifier.

9. The system of claim 8, wherein
the vapor fraction comprises a first portion of the butanes and the butenes;
the enriched solvent fraction comprises the 1,3-butadiene, the 1,2-butadiene, $C_4$ acetylenes, $C_3$ acetylenes, $C_{5+}$ hydrocarbons, and a second portion of the butanes and the butenes;
the rectifier overheads fraction comprises the second portion of the butanes and butenes
the rectifier side draw fraction comprises $C_3$ and $C_4$ acetylenes, 1,3-butadiene, 1,2-butadiene, and $C_{5+}$ hydrocarbons;
the rectifier bottoms fraction comprises a partially degassed solvent containing 1,2-butadiene and $C_4$ acetylenes
the degasser overheads fraction comprises 1,2-butadiene;
the degasser side draw fraction comprises $C_4$ acetylenes; and
the degasser bottoms fraction comprises degassed solvent.

10. The system of claim 8, further comprising:
- a separator for phase separating the compressed degasser overheads fraction to recover a condensate fraction; and
- a flow conduit for recycling at least a portion of the condensate fraction to the liquid ring compressor.

11. The system of claim 8, further comprising:
- a heat exchanger for heating the rectifier bottoms fraction via indirect heat exchange;
- a degasser feed drum for phase separating the heated rectifier bottoms fraction to produce a vapor phase and a liquid phase fed to the degasser.

12. The system of claim 11, wherein the degasser feed drum and the degasser are integral.

13. The system of claim 11, further comprising a heat exchanger for heating the liquid phase via indirect heat exchange upstream of the degasser.

14. The system of claim 11, wherein the heat exchanger for heating the rectifier bottoms fraction via indirect heat exchange comprises a heat exchanger for contacting the partially degassed solvent with the degasser bottoms fraction via indirect heat exchange.

15. The system of claim 14, wherein the heat exchanger for contacting the rectifier bottoms fraction comprises a suppressed vaporization heater.

16. The system of claim 8, further comprising a reboiler to supply heat to the rectifier via indirect heat exchange, wherein the reboiler comprises a single pass heat exchanger.

17. The system of claim 8, further comprising an afterwash column for separating solvent from the rectifier side draw and to recover a crude butadiene product stream.

18. The system of claim 7, further comprising a methyl acetylene distillation column for separating the crude butadiene product stream to recover an overheads fraction comprising acetylenes and a bottoms fraction comprising 1,3-butadiene, 1,2-butadiene, and heavier hydrocarbons.

19. The system of claim 18, further comprising a butadiene fractionator for separating the bottoms fraction from the methyl acetylene distillation column and to produce a 1,3-butadiene product stream.

* * * * *